US005528771A

United States Patent [19]

Yudin

[11] Patent Number: 5,528,771
[45] Date of Patent: Jun. 25, 1996

[54] BACK SUPPORT

[76] Inventor: Beniamin Yudin, 402 Marine Ave., #4A, Brooklyn, N.Y. 11209

[21] Appl. No.: 282,593

[22] Filed: Jul. 29, 1994

[51] Int. Cl.⁶ .................................. A61F 5/00; A61F 5/02
[52] U.S. Cl. .................... 602/19; 2/267; 2/311; 2/338; 2/44; 128/112.1; 128/113.1; 128/117.1
[58] Field of Search ................... 2/44, 92, 267, 2/311, 312, 338; 450/155, 156; 602/19; 128/112.1, 113.1, 117.1

[56] References Cited

U.S. PATENT DOCUMENTS

| | | | |
|---|---|---|---|
| 2,813,526 | 11/1957 | Beebe | 450/155 X |
| 4,627,109 | 12/1986 | Carabelli et al. | 2/44 |
| 4,805,243 | 2/1989 | Gibbens et al. | 2/228 |
| 5,105,473 | 4/1992 | Valtakari | 2/267 X |

FOREIGN PATENT DOCUMENTS 873575  7/1961  United Kingdom ............... 28/113.1

*Primary Examiner*—Jeanette E. Chapman
*Attorney, Agent, or Firm*—Ilya Zborovsky

[57] ABSTRACT

A back support to be worn by sufferers on their bodies comprises a patch of fur having a shape with a contour including an uppermost widest side, two lateral sides extending downwardly from the uppermost side and converging toward one another, and a smallest lower side connecting the lateral sides with one another, and means for holding the patch on a user's body.

7 Claims, 2 Drawing Sheets

FIG. 2
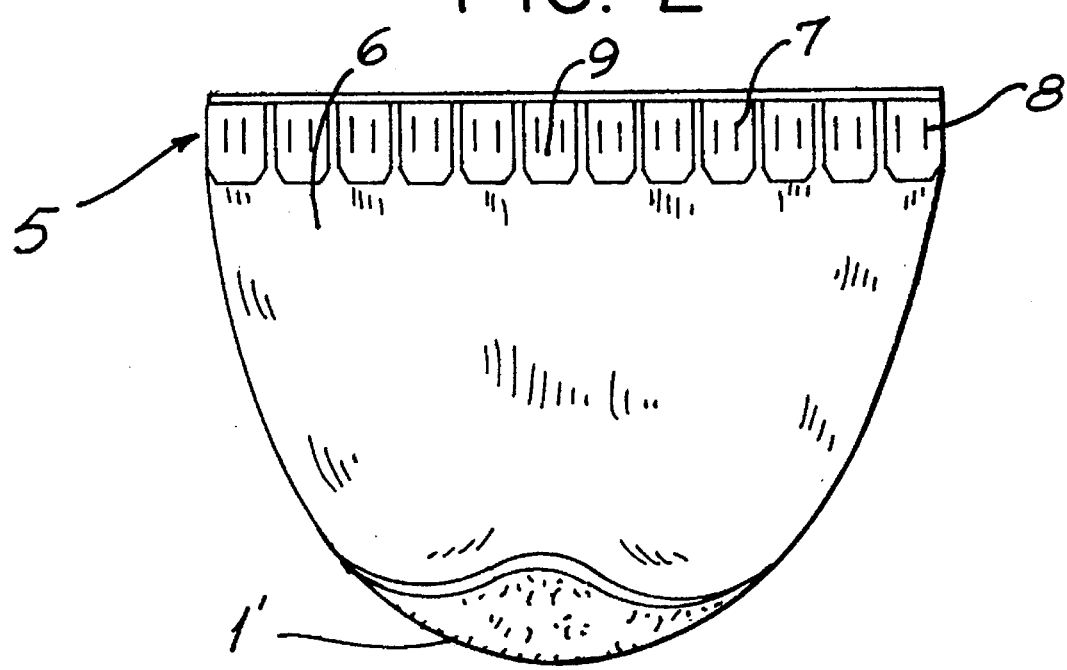
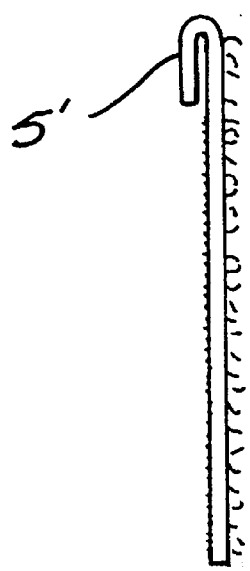
FIG. 3

BACK SUPPORT

BACKGROUND OF THE INVENTION

The present invention relates to a back support worn on the body of sufferers of lumbago or similar complaints.

Devices of such general type are known in the art. Some of such devices are disclosed for example in a Swedish patent 230232, U.S. Pat. Nos. 4,627,109, 4,702,235, 4,833,730, 4,926,502, 5,046,488, 5,179,942, French patent 975535. The above listed references disclose some devices, which however can be further improved for providing more efficient and fast pain alleviation.

SUMMARY OF THE INVENTION

Accordingly, it is an object of the present invention to provide a back support, which more efficiently alleviates pain of sufferers of lumbago or like complaints.

In keeping with these objects and with others which will become apparent hereinafter, one feature of the present invention resides, briefly stated, in a back support which in accordance with the present invention comprises a substantially heart-shaped patch of fur formed so that it can be applied to a lower thorax or waist region and also covers a coccus of a patient's body, and means for holding said patch on a user's body.

When the device is formed in accordance with the present invention with the above discussed substantially heart-shaped patch of fur, it provides for efficient pain alleviation for sufferers of lumbago or a like complaints.

The fur in question is natural fur which especially during wet and cold seasons protects user's skin from contact with air and warms the skin, and at the same time does not cause perspiration.

In accordance with a further feature of the present invention, the means for holding the patch on the user's body include a belt, and the patch has an upper wider portion fixed to and located completely on the belt while the lower narrower portion extends downwardly beyond the belt.

In accordance with still a further embodiment of the present invention, the means for holding the patch on the user's body include a folded over portion of the patch which is divided into a plurality of tongue portions each having two slots to form loops through which a belt or the like can extend.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 2 is a front view of a second embodiment of the inventive back support; and FIG. 3 is a side view of the device of FIG. 2.

DESCRIPTION OF THE PREFERRED EMBODIMENTS

Figure 1:
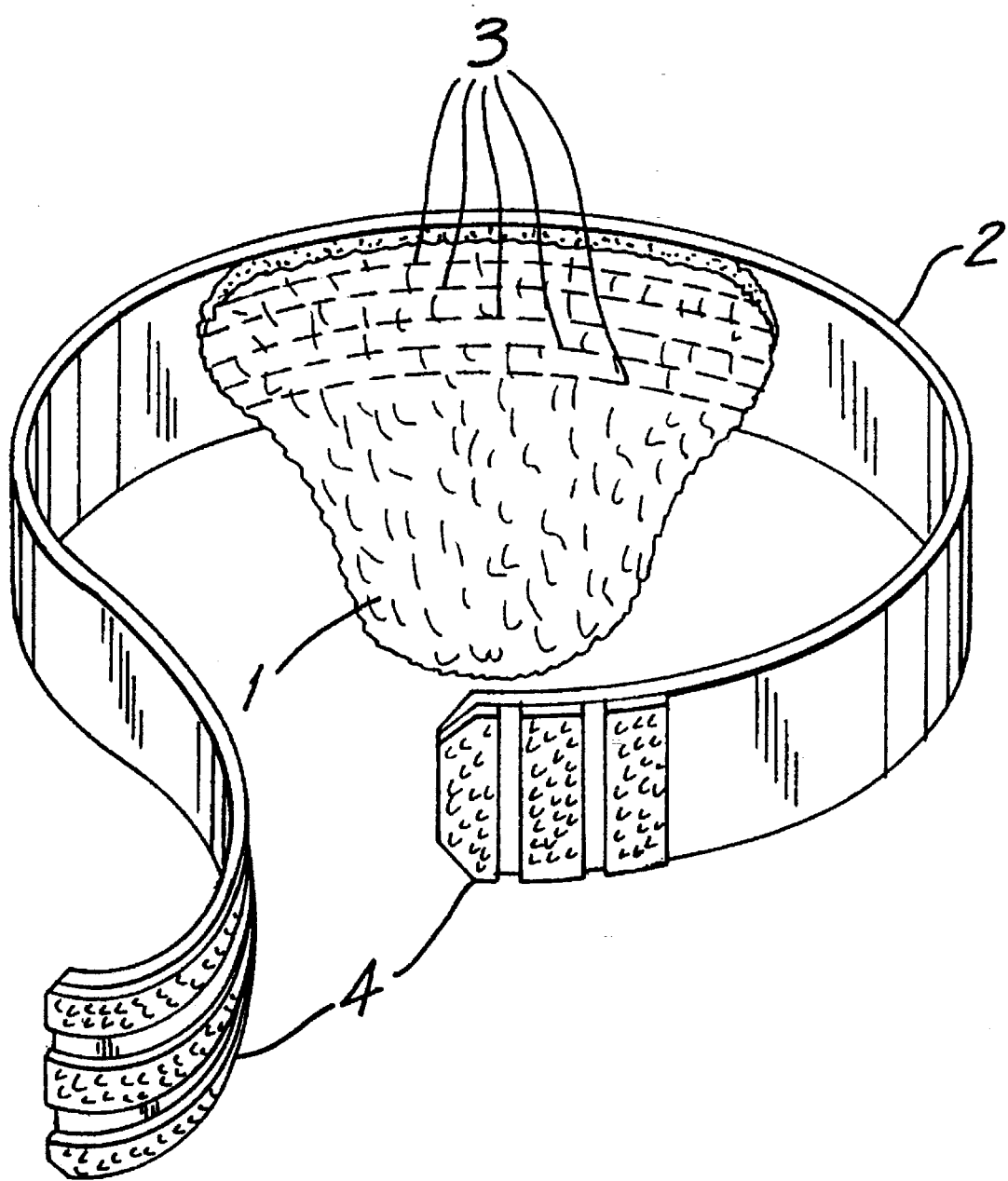
FIG. 1 is a perspective view of a back support in accordance with the first embodiment of the present invention.

A back support in accordance with the present invention as shown in FIG. 1 has a patch which is identified as a whole with reference numeral 1. The patch 1 is a fur patch which has front surface provided with fur hairs and a rear surface which does not have hair. Preferably, the patch 1 is made from fur of lamb, rabbit, long haired dogs, etc. The formation of the patch of natural fur is extremely important since it provides for highly efficient pain alleviation. The shape of the patch is also of especial inventive importance. The patch 1 is heart-shaped. In other words, it has a substantially triangular contour with a widest upper portion having rounded ends, narrowing concave sides extending from the upper widest portion, and a lower convex portion connecting the side concave portions with one another. This shape when applied on the user's back covers the area of the lower thorax or waist region of a patient's body, and also the area of the patient's coccus.

The device further has means for holding the patch on the user's body which is formed in the embodiment of FIG. 1 as a belt 2. The fur patch 1 is connected to the belt 2 by sewing, with the use of five seams 3 which extend parallel to the direction of elongation of the belt. The belt 2 is provided with locking means 4 arranged at its free ends. The locking means can be formed for example as a Velcro connection, including one piece formed with a plurality of projecting loops, and another piece formed with a plurality of hooks engageable with the loops.

As can be seen from FIG. 1, the upper widest portion of the patch is completely attached to the belt, while the intermediate and lower portions of the belt extend downwardly beyond the belt.

In order to use the device a user applies the patch onto his back area, extends the belt around his waist, and locks it by the locking means. The fur hairs are preferably placed in direct contact with the patient's skin. However, it is also possible to apply the patch with the hair in contact with the patient's underwear or in other words over the patient's underwear while the outer wear is applied on the device from the outer side.

In the second embodiment shown in FIGS. 2 and 3 the fur patch 1' has a somewhat different shape, in particular it has the upper widest portion, the intermediate portion with convex sides and a lower circular portion connecting the convex sides with one another. The fur patch 1' is also formed so that it can cover the lower thorax or waist region and also the coccus of a patient's body. The means for holding the patch 1' are also formed in a different manner. The holding means include a portion 5 which is bent over from the upper end of the patch downwardly and is subdivided by a plurality of slots 6 into individual tongues 7. Each tongue 7 is provided with two slots 8 so that an area between the two slots forms a loop 9. Preferably, eight tongues 7 can be provided.

In order to use the device, the patch is applied on the user's back, and a conventional belt can pass through the slots 8 of the tongues 7 or in other words underneath the loops 9 formed by the slots. The belt can pass in an alternating fashion over one tongue and then under an adjacent tongue. Also, the belt can be passed through the loops 9 formed in the tongues 7, and also through loops on user's clothes for example on user's pants, so that the device becomes attached to the user's clothes.

The device is very efficient in alleviating pain of sufferers of lumbago or like complaints. It can be used by any patients and also it is especially advisable to be used by drivers and other professionals who have to sit for hours uninterruptedly behind the steering wheel or in other situations.

It will be understood that each of the elements described above, or two or more together, may also find a useful application in other types of constructions differing from the types described above.

While the invention has been illustrated and described as embodied in a back support, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. A back support to be worn by sufferers on their bodies, comprising a patch of fur having a shape with a contour including an uppermost widest side, two lateral sides extending downwardly from said uppermost side and converging toward one another, and a smallest lower side connecting said lateral sides with one another so as to cover both user's waist region and coccus; and means for holding said patch on a user's body, said holding means including portion of said patch which is folded over a remaining portion of said patch and has a plurality of tongues separated from one another and each provided with two slots forming a loop therebetween so that a belt or a similar element can extend through said loops.

2. A back support as defined in claim 1, wherein said patch has an upper portion located adjacent to said upper side, said upper portion being substantially rectangular and having rounded ends.

3. A back support as defined in claim 1, wherein said lateral sides are substantially convex.

4. A back support as defined in claim 2, wherein said lateral sides are substantially convex.

5. A back support as defined in claim 2, wherein said lower side is substantially convex and round.

6. A back support as defined in claim 2, wherein said upper portion is attached to said means while a remaining portion of said patch extends downwardly beyond said means.

7. A back support as defined in claim 1, wherein said fur is a natural fur selected from the group consisting of a lamb fur, a rabbit fur and a long-haired dog fur.

\* \* \* \* \*